(12) United States Patent
 An et al.

(10) Patent No.: US 12,577,623 B2
(45) Date of Patent: Mar. 17, 2026

(54) METHOD FOR DETECTING COLORECTAL CANCER

(71) Applicant: GENOMICTREE, INC., Daejeon (KR)

(72) Inventors: Sungwhan An, Daejeon (KR); TaeJeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 831 days.

(21) Appl. No.: 17/765,515

(22) PCT Filed: May 22, 2020

(86) PCT No.: PCT/KR2020/015360
 § 371 (c)(1),
 (2) Date: Mar. 31, 2022

(87) PCT Pub. No.: WO2021/091239
 PCT Pub. Date: May 14, 2021

(65) Prior Publication Data
 US 2023/0002830 A1    Jan. 5, 2023

(30) Foreign Application Priority Data

Nov. 7, 2019    (KR) ........................ 10-2019-0141548

(51) Int. Cl.
| | |
|---|---|
| *C12Q 1/68* | (2018.01) |
| *C12Q 1/6886* | (2018.01) |
| *C12Q 1/6806* | (2018.01) |
| *C12Q 1/6851* | (2018.01) |

(52) U.S. Cl.
 CPC ......... *C12Q 1/6886* (2013.01); *C12Q 1/6806* (2013.01); *C12Q 1/6851* (2013.01); *C12Q 2600/154* (2013.01)

(58) Field of Classification Search
 CPC .. C12Q 1/6886; C12Q 1/6806; C12Q 1/6851; C12Q 2600/154; C12Q 2600/158
 See application file for complete search history.

(56) References Cited

U.S. PATENT DOCUMENTS

| | | | |
|---|---|---|---|
| 10,428,388 B2 * | 10/2019 | An | ....................... C12Q 1/6886 |
| 2016/0340740 A1 | 11/2016 | Zhang | |

FOREIGN PATENT DOCUMENTS

| | | |
|---|---|---|
| CN | 101622348 A | 1/2010 |
| CN | 104673896 A | 6/2015 |
| CN | 108410980 A | 8/2018 |
| JP | 2013509872 A | 3/2013 |
| JP | 2019501651 A | 1/2019 |
| KR | 1020180038252 A | 4/2018 |
| RU | 2630669 C1 | 9/2017 |
| WO | 2014062218 A1 | 4/2014 |
| WO | 2015116837 A1 | 8/2015 |

OTHER PUBLICATIONS

Evdokimov (Evdokimov et al.; Biology and Medicine, vol. 8, pp. 1-12, Oct. 7, 2016) (Year: 2016).*
Evdokimov (Evdokimov et al.; Biology and Medicine, vol. 8, pp. 1-12, Oct. 2016) (Year: 2016).*
GenBank Accession No. NM 144650 (Year: 2018).*
English Translation of Office Action issued in Japanese Patent Application No. 2022-526188 on May 23, 2023.
Office Action issued in Japanese Patent Application No. 2022-526188 on May 23, 2023.
Naumov, V.A., et al., "Genome-scale analysis of DNA methylation of colorectal cancer using Infinium HumanMethylation450 BeadChips", Epigenetics, 2013, pp. 921-934, vol. 8, No. 9.
EESR Issued in EP20885850.6 on Nov. 24, 2023.
Lam, K., et al., "DNA methylation based biomarkers in coloretal cancer: a systematic review", Biochimica et Biophysica Acta, 2016, pp. 106-120, vol. 1866, Publisher: Elsevier.
Ahlquist, D.A., et al., "Colorectal Cancer Screening by Detection of Altered Human DNA in Stool: Feasibility of a Multitarget Assay Panel", Gastroenterology, 2000, pp. 1219-1227, vol. 119, Publisher: American Gastroenterological Association.
Chen, J., et al., "DNA methylation biomarkers in stool for early screening of colorectal cancer", Journal of Cancer, 2019, pp. 5264-5271, vol. 10, No. 21, Publisher: IVYSPRING International Publisher.
Cross, S.H., et al., "CpG islands and genes", Current Opinion in Gene Development, 1995, pp. 309-314, vol. 5, Publisher: Current Biology Ltd.
Evdokimov, A. A., et al., "GLAD-PCR Assay of DNA Methylation Markers Associated with Colorectal Cancer", Biology and Medicine, 2016, pp. 1000342; DOI:10.4172/0974-8369.1000342, vol. 8, No. 7.

(Continued)

Primary Examiner — Jehanne S Sitton
Assistant Examiner — Bailey Buchanan
(74) Attorney, Agent, or Firm — HULTQUIST, PLLC; Steven J. Hultquist

(57) ABSTRACT

The present invention relates to a method for providing information for colorectal cancer diagnosis, a composition for diagnosing colorectal cancer, and a kit comprising same, and, more particularly, to: a method for providing information for colorectal cancer diagnosis by using a primer for specifically amplifying plural methylated colorectal cancer marker genes; a composition for diagnosing colorectal cancer; and a kit comprising same.

7 Claims, 4 Drawing Sheets
Specification includes a Sequence Listing.

(56)                    References Cited

OTHER PUBLICATIONS

Han, Y.D., et al., "Early detection of colorectal cancer based on presence of mythylated syndecan-2 (SDC2) in stool DNA", Clinical Epigenetics, 2019, Pages https://doi.org/10.1186/s13148-019-0642-0, vol. 11, No. 51.

Kim, Y-H, et al., "Epigenomic Analysis of Aberrantly Methylated Genes in Colorectal Cancer Identifies Genes Commonly Affected by Epigenetic Alterations", Annals of Surgical Oncology, 2011, pp. 2338-2347; DOI 10.1245/s10434-011-1573-y, vol. 18, Publisher: The Society of Surgical Oncology.

Offiice Action Issued in CN2020800776514 on Nov. 30, 2023.

English translation of Office Action issued in CN2020776514 on Nov. 30, 2023.

Search Report issued in CN2020800776514 on Nov. 29, 2023.

Huang, Z., et al., "Values of combined detection of polygene methylation in stool for the diagnosis of colorectal cancer and precancerous lesions", Cancer Research and Clinic, 2022, pp. 248-254, vol. 34, No. 4, Publisher: Chinese Medical Association.

Tae, C. H., et al., "Alcohol dehydrogenase, iron containing, 1 promoter hypermethylation associated with colorectal cancer differentiation", BMC Cancer, 2013, doi:10.1186/1471-2407-13-142, vol. 13, No. 142, Publisher: BioMed Central Ltd.

* cited by examiner

MeDIA-CpG microarray data

FIG. 4

| Sample # | Normal persons upon colonoscopy | | | | Sample # | Colorectal cancer patients | | |
|---|---|---|---|---|---|---|---|---|
| | COL2A1 | SDC2 | ADHFE1 | | | COL2A1 | SDC2 | ADHFE1 |
| 1 | 25.2 | Not detected | Not detected | | 1 | 24.9 | 29.4 | 28.8 |
| 2 | 25.3 | Not detected | Not detected | | 2 | 25.4 | 28.5 | 28.0 |
| 3 | 29.2 | Not detected | Not detected | | 3 | 24.3 | 23.6 | 24.2 |
| 4 | 25.5 | Not detected | 33.4 | | 4 | 23.5 | 28.7 | 27.2 |
| 5 | 28.1 | Not detected | Not detected | | 5 | 26.4 | 26.7 | 26.2 |
| 6 | 30.3 | Not detected | Not detected | | 6 | 24.2 | 28.6 | 24.8 |
| 7 | 29.4 | Not detected | Not detected | | 7 | 24.9 | 26.1 | 27.0 |
| 8 | 28 | Not detected | Not detected | | 8 | 25.4 | 25.5 | 24.2 |
| 9 | 25.1 | Not detected | Not detected | | 9 | 21.9 | 26.2 | 23.6 |
| 10 | 27.1 | Not detected | Not detected | | 10 | 23 | 25.3 | 25.6 |
| 11 | 30.2 | Not detected | Not detected | | 11 | 30.4 | Not detected | Not detected |
| 12 | 30 | Not detected | Not detected | | 12 | 26.8 | Not detected | 32.5 |
| 13 | 30.8 | Not detected | Not detected | | 13 | 30.8 | Not detected | Not detected |
| 14 | 31.6 | Not detected | Not detected | | 14 | 30.1 | Not detected | Not detected |
| 15 | 25.7 | Not detected | Not detected | | 15 | 25.1 | Not detected | Not detected |
| 16 | 27.3 | Not detected | Not detected | | 16 | 27.4 | Not detected | 31.9 |
| 17 | 30 | Not detected | Not detected | | 17 | 25.9 | Not detected | 26.6 |
| 18 | 31.5 | 31.5 | Not detected | | 18 | 29.7 | Not detected | 32.2 |
| 19 | 29.2 | Not detected | Not detected | | 19 | 30.3 | Not detected | 34.1 |
| 20 | 32 | Not detected | Not detected | | 20 | 26.9 | Not detected | 28.8 |
| 21 | 29.3 | Not detected | Not detected | | 21 | 27.7 | 32.5 | 31.6 |
| 22 | 28.4 | Not detected | Not detected | | 22 | 27.5 | 33 | Not detected |
| 23 | 28.4 | Not detected | Not detected | | 23 | 18.6 | 29.4 | 28.1 |
| 24 | 28.6 | Not detected | Not detected | | 24 | 22 | 25.8 | 24.6 |
| | | | | | 25 | 20.2 | 31.6 | 24.9 |
| | | | | | 26 | 22 | 33.4 | 26.7 |
| | | | | | 27 | 26.4 | 31.3 | 32.4 |
| | | | | | 28 | 23.9 | 28.9 | 29.8 |
| | | | | | 29 | 24.5 | Not detected | 31.7 |
| | | | | | 30 | 28 | Not detected | 34.1 |
| | | | | | 31 | 23.2 | Not detected | 26.2 |
| | | | | | 32 | 33.3 | Not detected | Not detected |
| | | | | | 33 | 30.9 | Not detected | Not detected |

```
                          SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Synthetic construct

<400> SEQUENCE: 1
agggtggatg gtgcgagc                                            18

<210> SEQ ID NO 2
<211> LENGTH: 19
<212> TYPE: DNA
<213> ORGANISM: Artificial Sequence
<220> FEATURE:
<223> OTHER INFORMATION: Synthetic construct

<400> SEQUENCE: 2
cctacccacc cgcttcgcg                                           19

<210> SEQ ID NO 3
<211> LENGTH: 30
<212> TYPE: DNA
<213> ORGANISM: Artificial Sequence
<220> FEATURE:
<223> OTHER INFORMATION: Synthetic construct

<400> SEQUENCE: 3
tgaggtttag ataggtgatt tcgcgaagcg                               30

<210> SEQ ID NO 4
<211> LENGTH: 18
<212> TYPE: DNA
<213> ORGANISM: Artificial Sequence
<220> FEATURE:
<223> OTHER INFORMATION: Synthetic construct

<400> SEQUENCE: 4
gtggatggtg cgagcgtc                                            18

<210> SEQ ID NO 5
<211> LENGTH: 23
<212> TYPE: DNA
<213> ORGANISM: Artificial Sequence
<220> FEATURE:
<223> OTHER INFORMATION: Synthetic construct

<400> SEQUENCE: 5
cgaccaatca cgaaaactac ccg                                      23

<210> SEQ ID NO 6
<211> LENGTH: 30
<212> TYPE: DNA
<213> ORGANISM: Artificial Sequence
<220> FEATURE:
<223> OTHER INFORMATION: Synthetic construct

<400> SEQUENCE: 6
cgtgggaaaa tggttttgag ttcgattggt                               30
```

-continued

```
<210> SEQ ID NO 7
<211> LENGTH: 26
<212> TYPE: DNA
<213> ORGANISM: Artificial Sequence
<220> FEATURE:
<223> OTHER INFORMATION: Synthetic construct

<400> SEQUENCE: 7
taggagtatt agtaatgtta ggagta                                            26

<210> SEQ ID NO 8
<211> LENGTH: 27
<212> TYPE: DNA
<213> ORGANISM: Artificial Sequence
<220> FEATURE:
<223> OTHER INFORMATION: Synthetic construct

<400> SEQUENCE: 8
ctttactacc ccaaaaaaac ccaatcc                                           27

<210> SEQ ID NO 9
<211> LENGTH: 27
<212> TYPE: DNA
<213> ORGANISM: Artificial Sequence
<220> FEATURE:
<223> OTHER INFORMATION: Synthetic construct

<400> SEQUENCE: 9
agaagaaggg aggggtgtta ggagagg                                           27

<210> SEQ ID NO 10
<211> LENGTH: 27
<212> TYPE: DNA
<213> ORGANISM: Artificial Sequence
<220> FEATURE:
<223> OTHER INFORMATION: Synthetic construct

<400> SEQUENCE: 10
gtagaaatta ataagtgaga gggcgtc                                           27

<210> SEQ ID NO 11
<211> LENGTH: 28
<212> TYPE: DNA
<213> ORGANISM: Artificial Sequence
<220> FEATURE:
<223> OTHER INFORMATION: Synthetic construct

<400> SEQUENCE: 11
acgactcaaa ctcgaaaact cgaactcg                                          28

<210> SEQ ID NO 12
<211> LENGTH: 22
<212> TYPE: DNA
<213> ORGANISM: Artificial Sequence
<220> FEATURE:
<223> OTHER INFORMATION: Synthetic construct

<400> SEQUENCE: 12
ttcggggcgt agttgcgggc gg                                                22
```

METHOD FOR DETECTING COLORECTAL CANCER

CROSS-REFERENCE TO RELATED APPLICATIONS

This is a U.S. national phase under 35 U.S.C. § 371 of International Patent Application No. PCT/KR2020/015360 filed May 22, 2020, which in turn claims priority under 35 USC § 119 of Korean Patent Application No. 10-2019-0141548 filed Nov. 7, 2019. The disclosures of all such applications are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "626_SeqListing_ST25.txt" created on Mar. 31, 2022 and is 2,571 bytes in size. The sequence listing contained in this .txt file is part of the specification and is hereby incorporated by reference herein in its entirety.

TECHNICAL FIELD

The present invention relates to a method of providing information for diagnosing colorectal cancer, a composition for diagnosing colorectal cancer, and a kit including the same, and more particularly to a method of providing information for diagnosing colorectal cancer using primers specifically amplifying a plurality of methylated colorectal cancer marker genes, a composition for diagnosing colorectal cancer, and a kit including the same.

BACKGROUND ART

In the genomic DNA of mammalian cells, a fifth base is present, in addition to A, C, G, and T, and is 5-methylcytosine (5-mC), in which a methyl group is attached to the fifth carbon of a cytosine ring. 5-mC is always attached only to C of a CG dinucleotide (5'-mCG-3'), and this CG is often denoted as CpG. The C in CpG is mostly methylated, with a methyl group attached thereto. This methylation of CpG inhibits the expression of repetitive sequences in the genome, such as Alu or transposons, and CpG is the site where extragenic changes most frequently occur in mammalian cells. 5-mC of this CpG is naturally converted into T through deamination. Accordingly, CpG appears in the mammalian genome with a frequency of only 1%, which is much lower than the normal frequency thereof ($\frac{1}{4} \times \frac{1}{4} = 6.25\%$).

There are regions called CpG sites (CpG islands) in which CpGs are exceptionally dense. A CpG site is 0.2-3 kb in length, and is a highly concentrated region in which the distribution percentage of C and G bases is greater than 50% and the distribution percentage of CpG is 3.75% or more. About 45,000 CpG sites appear in the entire human genome, and are intensively found in the promoter region, which regulates gene expression. Indeed, CpG sites appear in promoters of housekeeping genes, which account for about half of human genes (Cross S. et al., Curr. Opin. Gene Develop., 5:309, 1995). Abnormal DNA methylation is known to occur mainly in the 5' regulatory region of the corresponding gene, thereby reducing expression of the corresponding gene.

On the other hand, in somatic cells of normal persons, the CpG islands of these housekeeping gene promoter regions are not methylated, but imprinted genes and inactivated genes on the X chromosome are methylated so as to prevent expression thereof during development.

During the carcinogenesis process, methylation occurs in the promoter CpG island, and expression of the corresponding gene is impaired. In particular, when methylation occurs in the regulatory region CpG islands of tumor suppressor genes, which regulate cell cycles or apoptosis, repair DNA, participate in cell adhesion and intercellular interaction, and inhibit invasion and metastasis, the expression and function of these genes are blocked, like mutations in coding sequences, thereby promoting the development and progression of cancer. Partial methylation may also appear on CpG islands due to aging.

Regulatory region methylation of tumor-related genes is an important indicator of cancer, so it may be used in various ways, such as diagnosis and early diagnosis of cancer, prediction of cancer risk, prediction of cancer prognosis, follow-up after treatment, prediction of response to anticancer therapy, and the like. Indeed, recent attempts have been actively made to investigate the promoter methylation of tumor-related genes in the blood, sputum, saliva, stool, urine, and the like, and to use the results thereof in the treatment of various types of cancer (Ahlquist, D. A. et al., Gastroenterol., 119:1219, 2000).

Against this technical background, the inventors of the present application have ascertained that methylation of colorectal cancer marker genes may be detected with high detection limit and accuracy using primers specifically amplifying a plurality of methylated colorectal cancer marker genes, thus culminating in the present invention.

DISCLOSURE

It is an object of the present invention to provide a method of providing information for diagnosing colorectal cancer using primers specifically amplifying a plurality of methylated colorectal cancer marker genes.

It is another object of the present invention to provide a composition for diagnosing colorectal cancer using primers specifically amplifying a plurality of methylated colorectal cancer marker genes.

It is still another object of the present invention to provide a kit for diagnosing colorectal cancer including the composition.

In order to accomplish the above objects, the present invention provides a method of providing information for diagnosing colorectal cancer including (a) treating a sample with at least one reagent differently modifying methylated SDC2 (syndecan 2) and ADHFE1 (alcohol dehydrogenase iron-containing 1) genes and non-methylated SDC2 and ADHFE1 genes and (b) performing treatment with primers specifically amplifying the methylated SDC2 and ADHFE1 genes.

In addition, the present invention provides a composition for diagnosing colorectal cancer including at least one reagent differently modifying methylated SDC2 (syndecan 2) and ADHFE1 (alcohol dehydrogenase iron-containing 1) genes and non-methylated SDC2 and ADHFE1 genes and primers specifically amplifying the methylated SDC2 and ADHFE1 genes.

In addition, the present invention provides a kit for diagnosing colorectal cancer including the composition.

DESCRIPTION OF DRAWINGS

FIG. 4 shows the results of diagnosing colorectal cancer by detecting methylation of the SDC2 gene and methylation of the ADHFE1 gene in normal persons and colorectal cancer patients.

MODE FOR INVENTION

Figure 1:
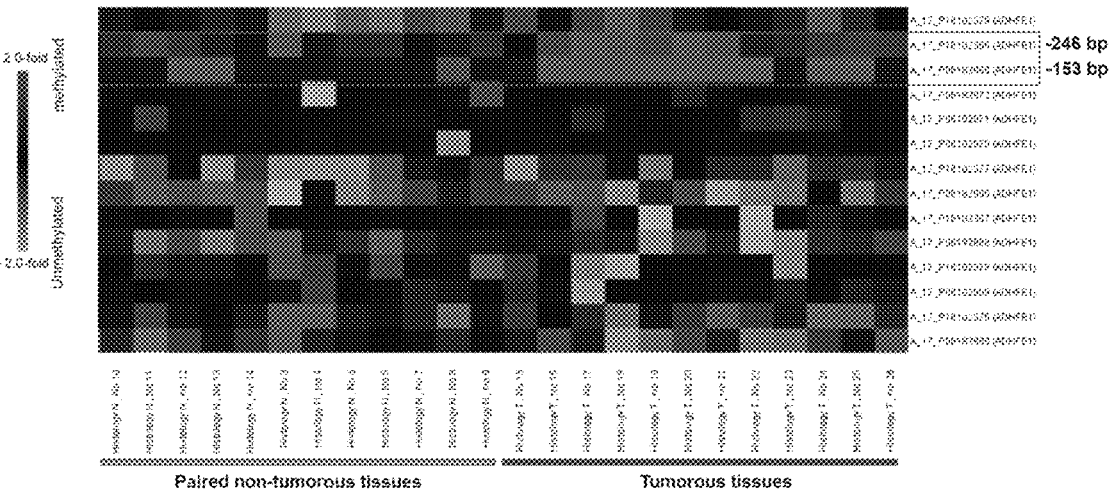
FIG. 1 shows the results of genome-level methylation analysis (MeDIA-CpG microarray) using cancer tissue of colorectal cancer surgery patients and normal tissue DNA adjacent thereto.

Unless otherwise defined, all technical and scientific terms used herein have the same meanings as those typically understood by those skilled in the art to which the present invention belongs. Generally, the nomenclature used herein is well known in the art and is typical.

The inventors of the present application have ascertained that the sensitivity and specificity of detection of methylated DNA may be improved using primers specifically amplifying a plurality of methylated colorectal cancer marker genes, compared to the extent of methylation detection based on a single colorectal cancer marker gene. In a specific embodiment according to the present invention, compared to the detection of methylation of the SDC2 gene, the sensitivity and specificity for colorectal cancer diagnosis were improved by detecting methylation of the SDC2 gene and the ADHFE1 gene, and thus usefulness in diagnosing colorectal cancer was high.

Accordingly, an aspect of the present invention pertains to a method of providing information for diagnosing colorectal cancer including (a) treating a sample with at least one reagent differently modifying methylated SDC2 (syndecan 2) and ADHFE1 (alcohol dehydrogenase iron-containing 1) genes and non-methylated SDC2 and ADHFE1 genes and (b) performing treatment with primers specifically amplifying the methylated SDC2 and ADHFE1 genes.

In the present invention, step (a) is treating the sample with at least one reagent differently modifying the methylated SDC2 and ADHFE1 genes and the non-methylated SDC2 and ADHFE1 genes.

As used herein, the term "methylation" means modification into 5-methylcytosine (5-mC), in which a methyl group is attached to the fifth carbon of a cytosine base ring, and 5-methylcytosine is always attached only to C of the CG dinucleotide (5'-mCG-3'), and this CG is often referred to as CpG. Methylation of CpG inhibits the expression of repetitive sequences in the genome, such as Alu or transposons, and CpG is the site where extragenic changes most frequently occur in mammalian cells. 5-mC of this CpG is naturally converted into T through deamination, and thus, CpG is present in the mammalian genome at a frequency of only 1%, which is much lower than the normal frequency thereof ($\frac{1}{4} \times \frac{1}{4} = 6.25\%$).

There are regions called CpG islands in which CpGs are exceptionally dense. A CpG island is 0.2-3 kb in length, and is a highly concentrated site in which the distribution percentage of C and G bases is greater than 50% and the distribution percentage of CpG is 3.75% or more. About 45,000 CpG islands appear in the entire human genome, and are intensively found in the promoter region, which regulates gene expression. CpG islands actually appear in promoters of housekeeping genes, which account for about half of human genes.

The nucleic acid isolated from a specimen is obtained from a biological sample of the specimen. In order to diagnose colorectal cancer or the progression of colorectal cancer, the nucleic acid has to be isolated from colorectal tissue by scraping or biopsy. Such a sample may be obtained through various medical procedures known in the art.

The extent of methylation of the nucleic acid of the sample obtained from the specimen is measured through comparison with the same portion of the nucleic acid from a specimen without a colorectal tissue cell growth abnormality. Hypermethylation indicates the presence of a methylated allele in at least one nucleic acid. When the same nucleic acid is tested in a specimen without a colorectal tissue cell growth abnormality, the methylated allele does not appear.

"Normal" cells are cells that do not show abnormal cell morphology or a change in cytological properties. "Tumor" cells are cancer cells, and "non-tumor" cells are cells that are part of the diseased tissue but are not the site of the tumor.

According to the present invention, early diagnosis of cell growth abnormalities in the colorectal tissue of a specimen is possible by determining the methylation stage of at least one nucleic acid isolated from the specimen. The methylation stage of at least one nucleic acid may be compared with the methylation stage of at least one nucleic acid isolated from a specimen not exhibiting abnormal colorectal tissue cell growth. Preferably, the nucleic acid is a CpG-containing nucleic acid such as a CpG island.

According to the present invention, it is possible to diagnose predisposition to cell growth abnormalities in the colorectal tissue of a specimen, including determining the methylation of at least one nucleic acid isolated from the specimen. The methylation stage of at least one nucleic acid may be compared with the methylation stage of at least one nucleic acid isolated from a specimen having no predisposition to abnormal cell growth in colorectal tissue.

As used herein, the term "predisposition" refers to the property of being susceptible to the above-mentioned cell growth abnormality. A specimen having a predisposition is a specimen which does not yet exhibit a cell growth abnormality but in which a cell growth abnormality is present or in which the likelihood of developing a cell growth abnormality is increased.

The presence of CpG methylation in target DNA may be an indicator of a disease, and, for example, CpG methylation of any one of a promoter, a 5' untranslated region, and an intron of target DNA may be measured.

The CpG-containing gene is typically DNA. However, the method of the present invention may be performed using a sample containing, for example, DNA, or DNA and RNA including mRNA, in which the DNA or RNA may be single-stranded or double-stranded, or a sample containing a DNA-RNA hybrid may be used.

A nucleic acid mixture may also be used. As used herein, the term "multiple" includes both the case in which there is a plurality of specific nucleic acid sequence sites to be detected in a gene and the case in which a plurality of target DNA sequences is included in one tube (a single reactor). The specific nucleic acid sequence to be detected may be a fraction of a large molecule, or may initially be present in the form of a discrete molecule in which the specific sequence constitutes the entire nucleic acid sequence. The nucleic acid sequence need not be a nucleic acid present in a pure form, and the nucleic acid may be a minor fraction of a complex mixture, such as one contained in whole human DNA.

Particularly, the present invention is directed to detecting methylation of a plurality of target DNA sequences in a sample in a single reactor, in which the sample may include multiple target DNA sequences, and any target DNA may be used without limitation, so long as it is a gene that affects the development or progression of colorectal cancer when expression thereof is suppressed due to abnormal methylation, as well as a control gene.

In the present invention, the sample may be derived from a human body, and the sample may include, for example, colorectal cancer tissue, cell, stool, urine, blood, serum, or plasma.

At least one reagent differently modifying the methylated DNA and the non-methylated DNA may be used without limitation, so long as it is able to distinguish between the non-methylated cytosine base and the methylated cytosine base, and examples of the reagent may include, but are not limited to, bisulfite, hydrogen sulfite, disulfite, and combinations thereof. Particularly, when treated with the reagent, the methylated cytosine base is not converted, and the non-methylated cytosine base may be converted into uracil or a base other than cytosine.

In the present invention, step (b) is performing treatment with primers specifically amplifying the methylated SDC2 gene and the methylated ADHFE1 gene.

For the primers, for example, forward and reverse primers may be paired and used simultaneously for PCR. The methylated "C" of the CpG region is necessarily positioned at the 3' end of the primers, thereby exhibiting high specificity for methylation detection. The forward primer specifically amplifying the methylated ADHFE1 gene may include, for example, the sequence of SEQ ID NO: 1 or 4. The reverse primer may include, for example, the sequence of SEQ ID NO: 2 or 5. The primer specifically amplifying the methylated SDC2 gene may include the sequence of SEQ ID NO: 10 or 11.

The present invention may further include performing treatment with a probe capable of complementary hybridization to each of the methylated SDC2 gene and the methylated ADHFE1 gene specifically amplified using the primers in step (b).

In a hybridization reaction, the conditions used to achieve a certain stringent level vary depending on the properties of the nucleic acid to be hybridized. For example, the length of the nucleic acid site to be hybridized, the extent of homology, the nucleotide sequence composition (e.g. GC/AT ratio), and the nucleic acid type (e.g. RNA, DNA) are taken into consideration in selecting the hybridization conditions. An additional consideration is whether the nucleic acid is immobilized on, for example, a filter or the like.

Examples of very stringent conditions are as follows: 2×SSC/0.1% SDS at room temperature (hybridization conditions), 0.2×SSC/0.1% SDS at room temperature (low-stringency conditions), 0.2×SSC/0.1% SDS at 42° C. (moderate-stringency conditions), and 0.1×SSC at 68° C. (high-stringency conditions). The washing process may be performed using any one of these conditions, and, for example, high-stringency conditions or any of the above conditions may be used. The conditions may be applied for 10 to 15 minutes each time in the order described above, or all or some of the conditions described above may be repeatedly applied. As described above, however, the optimal conditions vary depending on the particular hybridization reaction that is involved, and may be determined experimentally. Generally, high-stringency conditions are used for hybridization of the probe of interest.

The probe capable of complementary hybridization to the amplified methylated SDC2 gene may include, for example, the sequence of SEQ ID NO: 3 or 6. The probe capable of complementary hybridization to the amplified methylated ADHFE1 gene may include the sequence of SEQ ID NO: 12.

In some cases, the probe may be detectably labeled, and may be labeled with, for example, a radioactive isotope, a fluorescent compound, a bioluminescent compound, a chemiluminescent compound, a metal chelate, or an enzyme. Appropriate labeling of the probe as described above is a technique that is well known in the art, and may be performed through a typical method.

The amount of the amplification product may be detected based on a fluorescence signal. The detection method may include an intercalating method using an intercalator that exhibits fluorescence by binding to the double-stranded DNA of the amplification product to which the probe is bound, a method of using an oligonucleotide in which the 5' end is labeled with a fluorescent material and the 3' end is labeled with a quencher, or the like.

The amplification according to the present invention may be performed through real-time quantitative amplification, for example, real-time polymerase chain reaction (PCR), and in real-time PCR, the amount of a PCR amplification product may be detected using a fluorescence signal. As real-time PCR proceeds, the intensity of the fluorescence signal increases in proportion to the increase in the amount of the polynucleotide, and an amplification profile curve showing the intensity of the fluorescence signal depending on the number of amplification cycles is obtained.

In general, the amplification profile curve is divided into a baseline region, which shows a fluorescence signal in the background that does not substantially reflect the amount of polynucleotide, an exponential region, in which the fluorescence signal increases with an increase in the amount of a polynucleotide product, and a plateau region, in which PCR reaches saturation and thus the intensity of the fluorescence signal no longer increases.

Typically, the fluorescence signal intensity at the transition point from the baseline region to the exponential region, namely at the point at which the amount of the PCR amplification product reaches an amount detectable by fluorescence, is referred to as a threshold, and the number of amplification cycles corresponding to the threshold value on the amplification profile curve is referred to as a threshold cycle (Ct) value.

By measuring the Ct value, analyzing the standard curve in which the concentration is determined based on the Ct (threshold cycle) value for a standard material, and confirming the concentration of the amplified gene, methylation-specific sensitivity and/or specificity may be determined.

In one embodiment, the methylation may be detected using any method selected from the group consisting of PCR, methylation-specific PCR, real-time methylation-specific PCR, PCR using a methylated-DNA-specific binding protein, PCR using a methylated-DNA-specific binding antibody, quantitative PCR, gene chip, sequencing, sequencing by synthesis, and sequencing by ligation.

(1) Methylation-specific PCR: For detection by methylation-specific PCR, when treated with a bisulfate, the cytosine in the 5'-CpG'-3 region remains as cytosine in the case of methylation, and is converted into uracil in the case of non-methylation. Therefore, a primer corresponding to a region in which the 5'-CpG-3' nucleotide sequence exists may be constructed for the modified nucleotide sequence obtained after treatment with bisulfite. When PCR is performed using primers, in the case of methylation, a PCR product is made due to the use of the primers corresponding to the methylated nucleotide sequence, and methylation may be confirmed through agarose gel electrophoresis. Here, the methylation detection probe may be TaqMan, Molecular Beacon, or a probe having a self-reporting function or an energy-transfer labeling function, but is not limited thereto.

(2) Real-time methylation-specific PCR: Real-time methylation-specific PCR is a real-time measurement method modified from methylation-specific PCR, and includes treating genomic DNA with bisulfite, designing PCR primers corresponding to the methylated case, and performing real-time PCR using the primers. Here, there are two detection methods: a detection method using a TaqMan probe complementary to the amplified nucleotide sequence and a detection method using SYBR Green. Therefore, real-time methylation-specific PCR is capable of selectively quantitatively analyzing only methylated DNA. As such, a standard curve is created using an in-vitro methylated DNA sample, and a gene having no 5'-CpG-3' sequence in the nucleotide sequence is also amplified as a negative control for standardization, thus quantitatively analyzing the extent of methylation.

(3) PCR using methylated-DNA-specific binding protein, quantitative PCR, and DNA chip assay: In PCR using a methylated-DNA-specific binding protein or the DNA chip method, when a protein that specifically binds only to methylated DNA is mixed with DNA, the protein specifically binds only to methylated DNA, so methylated DNA may be selectively isolated.

In addition, methylation may be measured through quantitative PCR, and methylated DNA isolated with the methylated-DNA-specific binding protein is labeled with a fluorescent dye and hybridized to a DNA chip integrated with complementary probes, thereby measuring methylation.

(4) Detection of differential methylation bisulfite sequencing method: Another method of detecting a nucleic acid containing methylated CpG includes bringing a nucleic-acid-containing sample into contact with an agent that modifies non-methylated cytosine and amplifying the CpG-containing nucleic acid in the sample using CpG-specific oligonucleotide primers. Here, the oligonucleotide primers may be characterized in that the methylated nucleic acid is detected by distinguishing between modified methylated and non-methylated nucleic acids. The amplification step is optional and preferable, but not essential. This method relies on the PCR reaction to distinguish between modified (e.g. chemically modified) methylated DNA and non-methylated DNA.

(5) Bisulfite sequencing method: Another method of detecting a nucleic acid containing methylated CpG includes bringing a nucleic-acid-containing sample into contact with an agent that modifies non-methylated cytosine and amplifying the CpG-containing nucleic acid in the sample using methylation-independent oligonucleotide primers. Here, the oligonucleotide primers may be characterized in that the nucleic acid is amplified without distinguishing between modified methylated and non-methylated nucleic acids. The amplification product has been described in connection with bisulfite sequencing for detection of methylated nucleic acids by next-generation sequencing methods or for sequencing by the Sanger method using a sequencing primer.

(6) Next-generation sequencing methods include a sequencing-by-synthesis method and a sequencing-by-ligation method. These methods are characterized in that, instead of creating a bacterial clone, a single DNA fragment is spatially separated, amplified in situ (clonal amplification), and sequenced. Here, since hundreds of thousands of fragments are read simultaneously, such a method is also called a massively parallel sequencing method.

Basically, a sequencing-by-synthesis method is performed, a method of obtaining signals by sequentially attaching mono- or di-nucleotides is used, and examples thereof may include pyrosequencing, ion torrent, and Solexa methods.

Examples of NGS devices based on the sequencing-by-synthesis method include Roche's 454 platform, Illumina's HiSeq platform, Life Technology's Ion PGM platform, and Pacific BioSciences' PacBio platform. 454 and Ion PGM use emulsion PCR as a clonal amplification method, and HiSeq uses bridge amplification. The sequencing-by-synthesis method reads the sequence by detecting phosphate, protons, or pre-attached fluorescence generated when DNA is synthesized by sequentially attaching one nucleotide. In the method of detecting the sequence, 454 uses a pyrosequencing method using phosphate, and Ion PGM uses proton detection. HiSeq and PacBio detect fluorescence to decode the sequence.

A sequencing-by-ligation method is a sequencing technique using DNA ligase, which identifies nucleotides at certain positions in a DNA nucleotide sequence. Unlike most sequencing techniques using a polymerase, the sequencing-by-ligation method does not use a polymerase and is characterized in that DNA ligase does not ligate mismatched sequences. An example thereof is the SOLiD system. In this technique, two bases are read with spacing, which is repeated five times independently through primer reset, so accuracy is improved by reading each base twice in duplicate.

In the sequencing-by-ligation method, among the dinucleotide primer sets made of 16 combinations, dinucleotide primers corresponding to the nucleotide sequences are sequentially ligated, the combination of these ligations is finally analyzed, and the nucleotide sequence of the corresponding DNA is completed.

Here, the next-generation sequencing method may be exemplified by a sequencing-by-synthesis method or a sequencing-by-ligation method. The methylated-DNA-specific binding protein includes, but is not limited to, MBD2bt, and the antibody is a 5'-methyl-cytosine antibody, but is not limited thereto.

With regard to the primer used in the present invention, when a reagent such as bisulfite is used in step (a), the cytosine in the 5'-CpG'-3 site remains as cytosine in the case of methylation, and is converted into uracil in the case of non-methylation. Therefore, a primer corresponding to a region in which the 5'-CpG-3' nucleotide sequence exists may be constructed for the modified nucleotide sequence obtained after treatment with a reagent, such as bisulfite.

The primer may be constructed to have "substantial" complementarity with each strand of the gene locus to be amplified. This means that the primer has sufficient complementarity to hybridize with the corresponding nucleic acid strand under conditions for the polymerization reaction.

Another aspect of the present invention pertains to a composition for diagnosing colorectal cancer including at least one reagent differently modifying methylated syndecan 2 (SDC2) and ADHFE1 genes and non-methylated SDC2 and ADHFE1 genes and primers specifically amplifying the methylated SDC2 gene and the methylated ADHFE1 gene.

Since the components contained in the composition according to the present invention overlap the components described above, a description thereof applies equally thereto.

Still another aspect of the present invention pertains to a kit for detecting methylation of target DNA including the composition described above.

In one embodiment, the kit includes compartmentalized carrier means that accommodates a sample therein, a container including a reagent, and a container including a primer for each of the methylated SDC2 gene and the methylated ADHFE1 gene. In some cases, it may further include a container including a probe for detecting the product of amplification of each of the methylated SDC2 gene and the methylated ADHFE1 gene.

The carrier means is suitable for accommodating one or more individual containers, such as bottles and tubes, containing independent components for use in the method of the present invention. With regard to the specification of the present invention, one of ordinary skill in the art may readily determine the apportionment of the necessary agents in the containers.

A better understanding of the present invention may be obtained through the following examples. These examples are merely set forth to illustrate the present invention, and are not to be construed as limiting the scope of the present invention, as will be apparent to those skilled in the art.

Example 1. Selection of Colorectal-Cancer-Specific Methylation Gene ADHFE1

The present inventors performed genome-level methylation analysis (MeDIA-CpG microarray) using cancer tissue of 12 colorectal cancer surgery patients and normal tissue DNA adjacent thereto in order to search for genes that were specifically methylated in colorectal cancer, and thus reported 32 types of methylated genes in colorectal cancer (Oh et al., Journal of Molecular Diagnostics, 2013; 15(4): 498-507: Supplemental Table 1). Among these 32 genes, ADHFE1 (NM_144650, alcohol dehydrogenase iron-containing 1), which was highly methylated in colorectal cancer tissue, was selected as a colorectal-cancer-specific methylation gene (FIG. 1).

Example 2. Validation of Primer and Probe for ADHFE1 Methylation Detection

In order to construct a primer for detecting methylation of the ADHFE1 gene, methylation-specific primers and probes were designed using MethPrimer (http://www.urogene.org/cgi-bin/methprimer/methprimer.cgi) for the ADHFE1 gene sequence modified with bisulfite (Table 1).

TABLE 1

Primer and probe sequences for detecting ADHFE1 gene methylation

| Gene set | Primer | Sequence (5'→3') | SEQ ID NO: |
|---|---|---|---|
| ADHFE1 (Set 1) | F | AGGGTGGATGGTGCGAGC | 1 |
| | R | CCTACCCACCCGCTTCGCG | 2 |
| | Probe | [HEX]TGAGGTTTAGATAGGTGATTTCGCGAAGCG[BHQ1] | 3 |
| ADHFE1 (Set 2) | F | GTGGATGGTGCGAGCGTC | 4 |
| | R | CGACCAATCACGAAAACTACCCG | 5 |
| | Probe | [HEX]CGTGGGAAAATGGTTTTGAGTTCG ATTGGT[BHQ1] | 6 |
| COL2A1 | F | TAGGAGTATTAGTAATGTTAGGAGTA | 7 |
| | R | CTTTACTACCCCAAAAAAACCCAATCC | 8 |
| | Probe | [CY5]AGAAGAAGGGAGGGGTGTTAGGAGAGG[BHQ2] | 9 |

Figure 3:
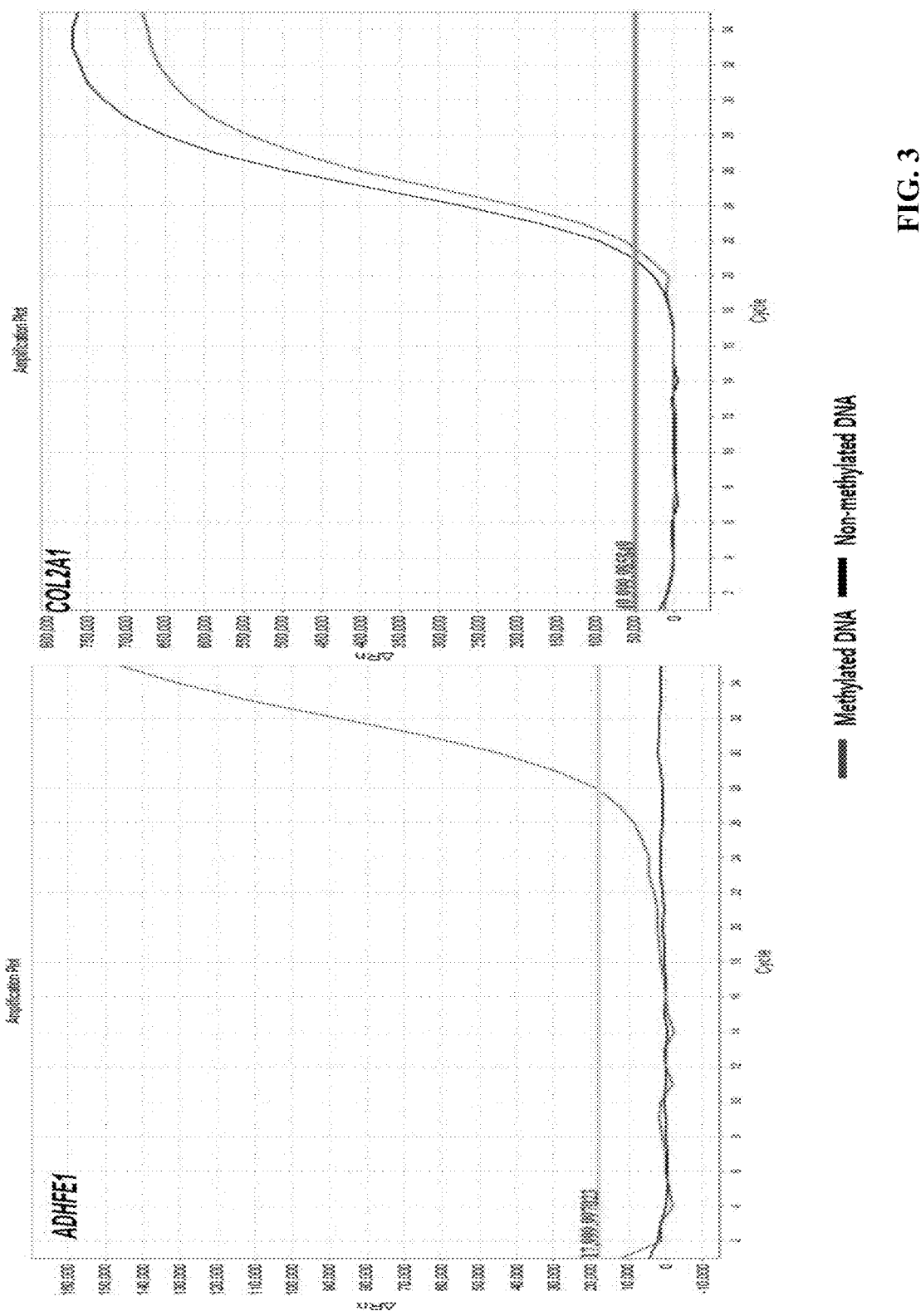
FIG. 3 shows the results of amplification using methylation-specific primers on the ADHFE1 gene.

In order to confirm the methylation-specific detection ability of the designed primers on the ADHFE1 gene, a quantitative methylation-specific real-time PCR (qMSP) method was performed using methylated and non-methylated control DNA (EpiTect PCR control DNA set (Qiagen, cat. no. 59695)). For qMSP, an AB 7500 Fast (Thermo Fischer) instrument was used. A total of 30 μl of a PCR reaction solution (20 ng/2 μl of template human DNA modified with bisulfite, 6 μl of 5× AptaTaq DNA Master (Roche Diagnostics), 2 μl (2.5 μmol/μl) of methylation-specific PCR primer (IDT, USA), 2 μl (2.5 μmol/μl) of TaqMan probe (IDT, USA), and 14 μl of DW) was prepared, and PCR was performed a total of 40 cycles under conditions of 95° C. for 5 minutes, 95° C. for 15 seconds, and then Methylation of SDC2 and ADHFE1 genes in stool DNA was measured using a total of 30 μl of a PCR reaction solution (2.0 μg/10 μl of stool DNA modified with bisulfite, 6 μl of 5× AptaTaq DNA Master (Roche Diagnostics), 2 μl (2.5 μmol/μl) of methylation-specific PCR primer (IDT, USA), 2 μl (2.5 μmol/μl) of TaqMan probe (IDT, USA), and 6 μl of DW), and the COL2A1 gene as an internal control gene was amplified therewith. PCR was performed a total of 40 cycles under conditions of 95° C. for 5 minutes, 95° C. for 15 seconds, and then 65° C. for 1 minute. Whether the PCR product was amplified was determined in real time (FIG. 3). Methylated and non-methylated control DNA (EpiTect PCR control DNA set (Qiagen, cat. no. 59695)) was used as a control and tested.

TABLE 2

| Primer and probe sequences for SDC2 gene methylation detection | | | |
| --- | --- | --- | --- |
| Gene | Primer | Sequence (5'→3') | SEQ ID NO: |
| SDC2 | F | GTAGAAATTAATAAGTGAGAGGGCGTC | 10 |
| | R | ACGACTCAAACTCGAAAACTCGAACTCG | 11 |
| | Probe | [FAM]TTCGGGGCGTAGTTGCGGGCGG[BHQ1] | 12 |

65° C. for 1 minute. Whether the PCR product was amplified was determined in real time. As an internal control gene, the COL2A1 gene was amplified therewith (FIG. 2).

Figure 2:
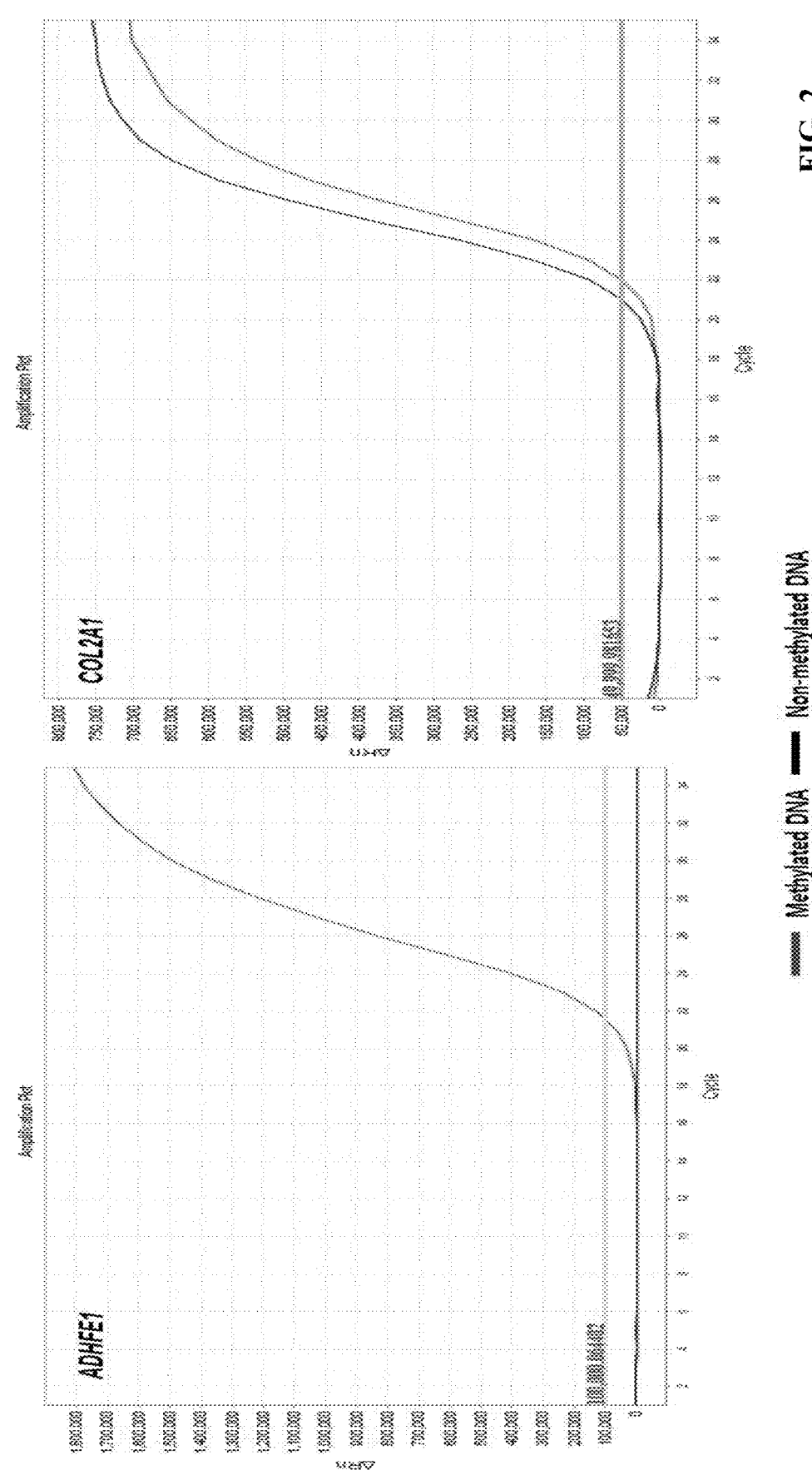
FIG. 2 shows the results of amplification using methylation-specific primers on the ADHFE1 gene.

As shown in FIG. 2, both ADHFE1 (Set 1) and the control gene COL2A1 were amplified in the methylated DNA, but in the non-methylated DNA, the ADHFE1 (Set 1) gene was not amplified and only the control gene COL2A1 was amplified, indicating that the methylation-specific primers on the ADHFE1 (Set 1) gene worked normally.

As shown in FIG. 3, both ADHFE1 (Set 2) and the control gene COL2A1 were amplified in the methylated DNA, but in the non-methylated DNA, the ADHFE1 (Set 2) gene was not amplified and only the control gene COL2A1 was amplified, indicating that the methylation-specific primers on the ADHFE1 (Set 2) gene worked normally.

Example 3: Increased Colorectal Cancer Diagnosis Performance Through SDC2 and ADHFE1 Gene Methylation Combination in Stool DNA In order to determine whether the ability to diagnose colorectal cancer was improved upon combination of methylation of the ADHFE1 gene and methylation of the SDC2 gene (Korean Patent No. 10-1142131), which is a conventional methylation biomarker for early diagnosis of colorectal cancer, methylation of the SDC2 gene was measured in 24 normal persons upon colonoscopy (Yonsei Medical Center Check-Up Center) and 33 colorectal cancer patients (Yonsei Medical Center, Colorectal and Anal Surgery) (FIG. 4). These specimens were previously measured for SDC2 methylation, and specimens in which positive SDC2 methylation was observed in 1 person out of 24 normal persons upon colonoscopy (4.2%) and was observed in 18 colorectal cancer patients (54.5%) were used.

Methylation measurement in these specimens was performed using the quantitative methylation-specific real-time PCR (qMSP) method described in Example 2. For qMSP, an AB 7500 Fast (Thermo Fischer) instrument was used, and an EZ Methylation Gold Kit (Catalog No. D5006, Zymo Research, USA) was used for modification with bisulfite.

When methylation of the ADHFE1 gene (Set 2) was measured in the stool of normal persons upon colonoscopy, positive methylation was observed in only 1 person (specificity of 95.8%), whereas positive methylation was observed in 26 colorectal cancer patients (sensitivity of 78.8%), indicating that it was effective at detecting colorectal cancer. In addition, upon combination of the ADHFE1 gene (Set 2) methylation and the previously known SDC2 gene methylation, a total of 2 normal persons upon colonoscopy including 1 additional person showed positive methylation, indicating that specificity was as high as 91.7%; that is, there was no significant impairment in specificity. Also, a total of 27 colorectal cancer patients including additional patients showed positive methylation, indicating that sensitivity was significantly increased to 81.8% (FIG. 4, P<0.033, Fisher's exact test).

INDUSTRIAL APPLICABILITY

According to the present invention, methylation can be detected with high detection sensitivity using primers specifically amplifying a plurality of methylated colorectal cancer marker genes, whereby the method of the present invention is capable of improving the ability to detect bowel cancer compared to a detection method using a single marker gene and of accurately and quickly diagnosing colorectal cancer, and is thus useful.

Although specific embodiments of the present invention have been disclosed in detail above, it will be obvious to those of ordinary skill in the art that the description is merely of preferable exemplary embodiments and is not to be construed as limiting the scope of the present invention. Therefore, the substantial scope of the present invention is to be defined by the appended claims and equivalents thereof.

SEQUENCE LIST FREE TEXT

An electronic file is attached.

The invention claimed is:

1. A method for detecting colorectal cancer by detecting CpG methylation of SDC2 (syndecan 2) and ADHFE1 (alcohol dehydrogenase iron-containing 1) genes, comprising:

(a) treating a nucleic acid sample comprising SDC2 and ADHFE1 genes with bisulfite to generate a bisulfite treated sample, and (b) contacting the bisulfite treated sample with (i) a primer pair consisting of SEQ ID NOs: 10 and 11, for amplifying methylated CpGs in SDC2, and (ii) a primer pair consisting of SEQ ID NOs: 1 and 2, or SEQ ID NOs: 4 and 5, for amplifying methylated CpGs in ADHFE1, wherein detection of CpG methylation of the bisulfite treated SDC2 and ADHFE1 genes is indicative of colorectal cancer.

2. The method according to claim 1, wherein at least one cytosine base is converted into uracil or a base different from cytosine through treatment with the bisulfite.

3. The method according to claim 1, further comprising (c) contacting the bisulfite treated sample with a probe capable of complementary hybridization to each of the methylated CpGs of the bisulfite treated SDC2 gene and the methylated CpGs of the bisulfite treated ADHFEI gene specifically amplified using the primer pairs (i) and (ii) in step (b).

4. The method according to claim 3, wherein the probe capable of complementary hybridization to the amplified methylated CpGs of the bisulfite treated ADHFEI gene comprises SEQ ID NO: 3 or 6.

5. The method according to claim 3, wherein the probe capable of complementary hybridization to the amplified methylated CpGs of the bisulfite treated SDC2 gene comprises SEQ ID NO: 12.

6. The method according to claim 1, wherein methylation is detected using a process selected from the group consisting of PCR, methylation-specific PCR, real-time methylation-specific PCR, PCR using a methylated-DNA-specific binding protein, PCR using a methylated-DNA-specific binding antibody, quantitative PCR, gene chip, sequencing, sequencing by synthesis, and sequencing by ligation.

7. The method according to claim 3, wherein methylation is detected by a material that binds to the probe and exhibits fluorescence.

\* \* \* \* \*